United States Patent [19]

Jabourian

[11] Patent Number: 5,695,343
[45] Date of Patent: Dec. 9, 1997

[54] METHOD FOR ESTIMATING THE LEVEL OF THE INTELLECTUAL FUNCTIONS OR THE PSYCHOMOTOR POTENTIAL OF A PERSON

[76] Inventor: Artin-Pascal Jabourian, 23, boulevard Beauséjour, 75016 Paris, France

[21] Appl. No.: 563,534

[22] Filed: Nov. 28, 1995

[51] Int. Cl.⁶ .................................................. G09B 19/00
[52] U.S. Cl. ............................................ 434/236; 434/237
[58] Field of Search ................................... 434/236, 237

[56] References Cited

PUBLICATIONS

Sato et al.; Correlation Between Exercise and Psychiatric Function in Aged Patients with Circulatory Disease; Tairyoku Kagaku vol.40, No. 1,pp. 121–126, 1991.

Barclay et al. . . . : Unrecognized Cognitive Impairment in Cardiac Rehabilitation Patients. J.Am.Geriatr.Soc. 36(1):22–30, 1988.

Jabourian, A.P., "Fonctions Cognitives, EEG et troubles de la Marche dans les Arythmies Cardiaques, un Jour Avant et Huit Jours aprés l'Implantation d'un Stimulateur Cardiaque," *Annales Médico Psychologiques*, vol. 153, No. 2, Feb. 1995, pp. 89–105.

*Primary Examiner*—Richard J. Apley
*Assistant Examiner*—John Rovnak
*Attorney, Agent, or Firm*—Pollock, Vande Sande & Priddy

[57] ABSTRACT

A method diagnoses cognitive impairment in an individual, otherwise free of neurological lesions or orthopedic difficulties of the lower limbs. Preliminarily, a reference group of persons is subjected to at least one physical test, requiring an observed walk along a path of predetermined length, and a plurality of psychometric tests indicative of cognitive function-for establishing a database of the relations between the psychometric test and the physical test for each person of the group. After establishment of the database, the individual undergoing diagnosis is subjected to the same physical test as given to the persons of the group. The results are compared solely on the basis of the physical test of the individual relative to the database, for deducing the individual's likely corresponding psychometric test result.

12 Claims, No Drawings

METHOD FOR ESTIMATING THE LEVEL OF THE INTELLECTUAL FUNCTIONS OR THE PSYCHOMOTOR POTENTIAL OF A PERSON

FIELD OF THE INVENTION

The invention is directed to evaluation of the level of intellectual functions or psychomotive potential of a person who, a priori, does not have any characterized neurological lesions (ie. which are identified and for which the person is receiving medical care), or orthopedic troubles of the lower limbs.

BACKGROUND OF THE INVENTION

It must be possible to carry out an evaluation of this type simply, without particular stress for the person in question, and using a device which is easy to install and use.

Various previous works have been undertaken in order to attempt to define the relationships which can exist between the cognitive functions and troubles in walking, in particular for people who may suffer from cardiac arrhythmia.

Thus, in the "Annales médico-psychologiques" (Medical-psychological annals). volume 153, February 1995, no. 2, pages 89 to 105, A. P. JABOURIAN published a report on "cognitive functions, electroencephalograms, and troubles with walking in cases of cardiac arrhythmia, one day before and eight days after implantation of a cardiac stimulator".

This publication describes in particular psychometric tests (FOLSTEIN's MMSE, BENTON's visual retention test, and REY's figure test with its two sub-tests known as REY C and REY M). Reference is also made to evaluation of the speed of walking of the patients examined, by timing along a single specific path.

There is now also available a device, the "statokinogram", which permits measurement of the center of gravity, the muscular tonus or the postural tonus of a person in different situations, thus allowing detailed analysis of the various stages of deportment and walking.

However this device can be used only in a specialized laboratory, and its use is limited to analysis of the various parameters involved in the study of the physical balance of a person.

In other words, until now, no method has been proposed for evaluating the capacity of a person to carry out given tasks, and which can help a medical practitioner to evaluate any intellectual deficit, on the basis of one or more tests which, although they are simple, reveal reliably the level of the intellectual functions or psychomotive potential of this person.

BRIEF DESCRIPTION OF THE INVENTION

The solution according to the invention is as follows:

individuals in a reference group which has varied intellectual functions (preferably ranging from normal to demented) are submitted to at least one physical test which corresponds to movement on foot along a predetermined path, and at least one psychometric test to evaluate the cognitive functions;

the results of the tests of each individual in this group are recorded in order to obtain reference data which is stored, for example, in a computer memory;

then, when it is necessary to evaluate further the intellectual capacities of a given person, that person is subjected to the aforementioned physical test(s), and on the basis of the test result(s), and by comparison with the said reference data, there is deduced the result which the person should have according to the psychometric test(s) undergone by the reference group, in order, using the methods of specialist practitioners, to evaluate the said intellectual capacities of this person (since a direct ratio exists between the result of one or more psychometric tests and this level of capacities).

As a physical test, the reference group and the person "to be evaluated" are subjected, preferably along a common walking path only, for example, of fifty meters, to a single test of this type which has the advantage of not being "stressful", or difficult to conduct or undergo, and the time taken in order to travel along the path is then measured. As additional information, the number of steps, the speed, and the average size of the steps can also be recorded.

DETAILED DESCRIPTION OF THE INVENTION

In order to obtain additional "physical" information, it can also be decided to equip the individuals in the reference group and the person to be evaluated with muscular tension sensors disposed in at least some of the following places: neck, arm, back, body, legs, cervical rachis, in order to obtain information concerning posture and balance. It will be appreciated that the measurements provided by the sensors during a physical test (which could be the aforementioned walking test or another test) are recorded. Account is then taken of all the physical data gathered, in order, by comparison with the reference data, to deduce the result which the person involved in the psychometric tests should have (and to which the person has thus not been submitted).

As cognitive function psychometric tests sustained by the reference group, the following well-known tests in particular can be used: WELSCHLER-BELLEVUE's test, WAIS' test, test PM 38, test D48, vocabulary test, BINET-SIMON's test, REY's tests (REY C, REY M), BENTON's test, MMSE test.

It should be noted that the comparison made within the context of the present invention, between troubles with walking and intellectual or cognitive functions, has already been found to be conclusive, particularly for people aged 60 or more, and more specifically over 65. On the other hand, it is considered that for younger people, the speed of walking is probably not the only criterion, or at least a sufficient criterion, in order to evaluate their intellectual functions: movement on foot, and in particular walking, is a reflection of the depressive or elated emotional state of the person. The posture of a person who is depressed is, for example, habitually characterized by slumped shoulders and lowered head, with general psychomotive sluggishness in which slowness of walking is only one factor.

Thus, if the method according to the invention is to be used on people aged less than 60 to 65, it is advisable to complement the psychometric tests taken both by the reference group (at least the majority of which will thus be selected from the age group in question) and by the person of whom the intellectual capacities or extent of psychomotive troubles are to be evaluated, by personality or projective tests to investigate the affective and/or emotional field, such as RORSCHACH's test, the TAT test, the "Multiparametric Minnesota Personality Inventory" personality test, MMPI, the projective tests for children known as the CAT tests, the BLOT test, or HAMILTON's test (for anxiety/depression).

Under these conditions, for the people concerned, conduction as physical tests of a test of movement on foot (such as a walking test for thirty to fifty meters), with recording (which can be concurrent) of the results provided by the aforementioned muscular tension sensors, will provide the conclusive results required on evaluation of the intellectual functions and emotional or thymic functions of the person.

Irrespective of the age of the individuals concerned, it can be useful to take into account an additional factor, i.e. the sex of the person.

Hereinafter, a practical example of application of the invention is described:

let us consider firstly a group which has undergone a common walking test of fifty meters, as well as four psychometric tests, i.e. REY C (copying REY), REY M (memory REY), MMSE and BENTON's test.

The results recorded are given in the following table.

TABLE A

| | | PSYCHOMETRY | | | | WALKING |
|---|---|---|---|---|---|---|
| AGE | SEX | REY C | REY M | MMSE | BENTON | TOTAL | for 50 m (in seconds) |
| 57 | F | 36 | 13 | 28.5 | 12 | 89.5 | 38 |
| 36 | F | 36 | 16 | 29 | 28 | 109 | 35 |
| 59 | F | 36 | 11 | 30 | 22 | 99 | 40 |
| 74 | M | 36 | 12 | 29 | 28 | 105 | 38 |
| 72 | F | 36 | 18 | 30 | 24 | 108 | 40 |
| 55 | F | 35 | 29 | 24.5 | 22 | 110.5 | 45 |
| 50 | M | 36 | 30 | 30 | 14 | 110 | 28 |
| 79 | F | 30 | 4 | 26.5 | 12 | 72.5 | 40 |
| 67 | F | 30 | 2 | 27 | 22 | 81 | 40 |
| 67 | F | 21 | 4 | 11 | 12 | 48 | 58 |
| 73 | F | 15 | 2 | 20 | 6 | 43 | 110 |
| 73 | F | 30 | 4 | 30 | 22 | 86 | 48 |
| 60 | F | 35 | 2 | 30 | 22 | 89 | |
| 89 | M | 35 | 17 | 27.5 | 14 | 83.5 | 42 |
| 69 | F | 20 | 5 | 28 | 8 | 61 | 50 |
| 58 | F | 35 | 11 | 25.5 | 20 | 91.5 | 32 |
| 47 | F | 34 | 13 | 29 | 22 | 98 | 35 |
| 64 | F | 33 | 18 | 28 | 18 | 97 | 38 |
| 69 | F | 26 | 9 | 28 | 18 | 81 | 60 |
| 59 | F | 36 | 18 | 29 | 26 | 109 | 32 |
| 36 | F | 36 | 13 | 27.5 | 26 | 102.5 | 34 |
| 29 | M | 34 | 18 | 29 | 22 | 103 | 33 |
| 74 | M | 35 | 18 | 23.5 | 24 | 100.5 | 55 |
| 80 | F | 30 | 6 | 26.5 | 16 | 78.5 | 65 |
| 70 | F | 30 | 19 | 29 | 20 | 98 | 31 |
| 44 | F | 35 | 12 | 30 | 24 | 101 | 28 |
| 70 | F | 34 | 14 | 29 | 22 | 99 | 38 |

This group (which can naturally be expanded, but the usefulness of which in this case is simply to illustrate the method according to the invention) thus provides information concerning firstly the intellectual functions of the individuals which constitute it (via the results of the psychometric tests which reveal the level of these functions), and secondly their physical capacities (results of the walking test), with two possible elements of correction, i.e. age and sex.

As already stated, further data could be added (in particular if the reference group is aged less than 60 to 65), i.e. results of projective tests and muscular tension sensor records, enabling posture and physical balance to be taken into consideration.

In all cases, after conventional statistical processing, the table below permits determination of the following standard deviations (for each psychometric test and for the total of these test, then for the walking test):

| Psychometric test | | | | | Physical test St. Dev. |
|---|---|---|---|---|---|
| St. Dev. REY C | St. Dev. REY M | St. Dev. MMSE | St. Dev. BENTON | St. Dev. TOTAL | WALKING (in seconds) |
| 5.4225 | 7.9421 | 3.9119 | 5.8859 | 30.3917 | 16 |

In terms of individual averages and total average, the results are also as follows:

| AV. REY C | AV. REY M | AV. MMSE | AV. BENTON | AV. TOTAL | AV. WALKING (in seconds) |
|---|---|---|---|---|---|
| 32.2414 | 13.1724 | 27.1964 | 19.4815 | 81.3906 | 42 |

Again, by means of conventional statistical calculation, error probabilities can be obtained per test and for all of the psychometric tests, as follows: $p<0.001$ for each copying REY, memory REY, MMSE and BENTON test, and $p<0.05$ for the total score of the cumulative results of the psychometric tests.

These results are encouraging, particularly since this type of table, which enables "intellectual" (psychometric) scores to be compared with "physical" scores, according to the inventor also reveals that if the time taken by the individual concerned to carry out the physical test selected is greater than the average time by about 1.5 to 2 standard deviations (i.e. in this case approximately 63 to 84 s), it can be postulated with a reasonable degree of certainty that the probable intellectual deficit which will be determined on reading the (or at least some of the) associated psychometric tests is derived from an extracerebral organic cause. Cardiopathy caused by troubles of the cardiac rhythm must be envisaged in particular, especially in the case of elderly people whose walking has slowed down considerably. An example of this is the 11th case in table A. Mrs X, aged 73, with a psychometric total of 43, and a walking time of 110 s.

In practice, the data in table A can advantageously be recorded in the memory of a computer, such as to facilitate subsequent "deductive evaluation" of the person, the level of whose cognitive functions are to be determined.

In fact, at that point, it will be sufficient to enter also in the computer the result of this person in the walking test (in this case the only physical test applied) along the same fifty meter path as that in table A.

If for example the person walks the distance in 38 seconds, is aged 71 and is male, it can be deduced that this person should reasonably have a total psychometric score of about 105 (corresponding to the fourth individual in the table) in the aforementioned four tests. The method can, however be improved further still by proceeding according to linear interpolation (or another known mathematical method), and for this purpose getting the computer to carry out a calculation which takes into account the age and result for a given test or for the cumulation of several tests. Thus, for example, the results obtained can be selected for the fourth and fourteenth individuals, or for all the individuals who obtained the same time in the walking test, irrespective of their age and sex. However this is simply a matter of conventional mathematical processing which can easily be carried out by a suitable computer program, and is all the more reliable the larger the number of individuals in the reference group and the more "varied" their intellectual functions.

In the above-described example, it could, for example, be deduced that the person to be evaluated should have a cumulative score of 100 or 102, rather than 105.

In practice, it is probable that this will not greatly affect evaluation of the level of the person's intellectual functions.

Whatever the case, although this psychometric "score" is a result which can be used by a specialist such as a neuro-psychiatrist, it is not explicit for another doctor or patient.

Consequently, there is provided hereinafter an interpretive table consisting of a type of "psychomotive scale" or "behavior table", which is intended to help the practitioner to evaluate in practice the behavioral capacities of the person in question and/or enlighten this person or people involved with the latter concerning the person's capacities.

This table is as follows:

TABLE B

Overall result of the psychometric tests in Table A.

0–5: PROFOUND DEMENTIA

No communication; all the intellectual faculties are impaired; cannot carry out simple tasks such as using a knife and fork or the telephone; cannot get dressed, wash or walk unaided; physical deterioration; in bed most of the time; requires major, continual assistance.

5–20: SEVERE DEMENTIA

Major disorder of memory and orientation; simple daily activities such as using a knife and fork or the telephone can be carried out more or less correctly; dressing, washing and walking require help; little or no physical deterioration; requires intermittent assistance; however cannot live alone.

20–60: "SIMPLE" DEMENTIA

Can live at home or in a family structure; does not go out alone; no longer travels alone on public transport; cannot do shopping, or can only do so with difficulty; can call known telephone numbers.

60–90: INTELLECTUAL DECLINE

Apparent only in professional life or in psychological or psychometric tests; social and family life possible.

90 or over: NO DECLINE

Normal professional life.

Thus if the person selected as the reference has a score of approximately 100 or 105, in both cases this person is considered to be free from dementia and intellectual decline, and must be considered suitable for leading a normal professional life.

If on the other hand a total score of 25 is deduced from table A, table B indicates "simple" dementia, with a series of information concerning the psychomotive capacities of this person.

It should be noted the comparison of the result in the walking test, and the score of one or more individual tests (REY, MMSE etc) rather than the total psychometric score as above, is also advisable.

It should also be noted that taking this into account, it is perfectly possible to produce table B from the results of the psychometric tests taken individually.

Additionally, it should be noted that the physical test(s) can be conducted for a longer period of time than that taken to travel the 50 meters referred to. Ambulatory wearing of one or more sensors/recorders whilst walking (and more generally living "normally") would then be appropriate.

I claim:

1. A method for diagnosing cognitive impairment in an individual that is free of neurological lesions or orthopedic difficulties of the lower limbs, comprising the steps:

preliminarily subjecting a reference group of persons to at least one physical test including a predetermined measured physical movement on foot and at least one psychometric test indicative of cognitive function for establishing a database of the relations between the psychometric test and the physical test for each person of the group;

subjecting the individual undergoing diagnosis to the same measured physical test as given to the persons of the group; and comparing the results of solely the physical test of the individual to the database for deducing the individual's likely corresponding psychometric test result.

2. The method set forth in claim 1 further comprising the establishment of a behavior table from the database, listing various behavioral difficulties as a function of psychometric test score, the table listing at least two of the following difficulties: profound dementia, severe dementia, simple dementia, intellectual decline, and lack of intellectual decline; and classifying the individual's behavioral difficulty on the basis of the individual's likely corresponding psychometric test result.

3. Method according to claim 2, in which the said psychometric tests comprise cognitive tests and projective tests which investigate the emotional and affective domain of the individual.

4. Method according to claim 2, in which at least the time taken to travel the path is recorded during the walking test.

5. The method set forth in claim 1 further comprising the steps of:

establishing a standard deviation and an average for the physical test in the database;

in the event the physical test of the individual undergoing diagnosis exceeds 1.5 standard deviations higher than the average; and if the database indicates that the individual is likely to have cognitive impairment;

concluding that the cognitive impairment has an extracerebral organic cause.

6. Method according to claim 5, wherein the extracerebral organic cause is a cardiopathy.

7. Method according to claim 5, wherein the extracerebral organic cause is a cardiac arrhythmia.

8. A method for diagnosing cognitive impairment in an individual that is free of neurological lesions or orthopedic difficulties of the lower limbs, comprising the steps:

preliminarily subjecting a reference group of persons to at least one measured physical test requiring an observed walk along a path of predetermined length and a plurality of psychometric tests indicative of cognitive function for establishing a database of the relations between the psychometric test and the physical test for each person of the group;

subjecting the individual undergoing diagnosis to the same measured physical test as given to the persons of the group; and comparing the results of solely the physical test of the individual to the database for deducing the individual's likely corresponding psychometric test result.

9. The method set forth in claim 8 wherein a majority of group persons as well the individual are over 60 years of age; and further wherein the individual and each person of the group are free of cardiopathy.

10. The method set forth in claim 8 further comprising the step of subjecting the persons of the group to a predetermined additional physical test;

recording data in the database, from muscular tension sensors mounted on at least one of the following body parts of each of the persons of the group-neck, arm, back, legs, and cervical rachis, in order to obtain information regarding posture and balance;

mounting similar sensors to the individual undergoing diagnosis to obtain corresponding data;

comparing the results of solely the physical tests of the individual to the database for deducing the individual's likely corresponding psychometric test result.

11. The method set forth in claim 8 wherein the observed walk is accompanied by recordal of the following information: time for completion, number of steps taken, speed, and size of steps.

12. The method set forth in claim 8 wherein the database includes data relating to the sex of persons of the group; and further wherein comparing the results is additionally a function of the sex of the individual.

* * * * *